(12) United States Patent
Giakos

(10) Patent No.: US 7,823,215 B2
(45) Date of Patent: Oct. 26, 2010

(54) MOLECULAR IMAGING AND NANOPHOTONICS IMAGING AND DETECTION PRINCIPLES AND SYSTEMS, AND CONTRAST AGENTS, MEDIA MAKERS AND BIOMARKERS, AND MECHANISMS FOR SUCH CONTRAST AGENTS

(75) Inventor: George C. Giakos, Fairlawn, OH (US)

(73) Assignee: The University of Akron, Akron, OH (US)

( * ) Notice: Subject to any disclaimer, the term of this patent is extended or adjusted under 35 U.S.C. 154(b) by 347 days.

(21) Appl. No.: 11/912,560

(22) PCT Filed: May 12, 2006

(86) PCT No.: PCT/US2006/018403

§ 371 (c)(1),
(2), (4) Date: May 9, 2008

(87) PCT Pub. No.: WO2006/124572

PCT Pub. Date: Nov. 23, 2006

(65) Prior Publication Data

US 2009/0119808 A1 May 7, 2009

Related U.S. Application Data

(60) Provisional application No. 60/680,461, filed on May 12, 2005, provisional application No. 60/680,460, filed on May 12, 2005.

(51) Int. Cl.
G01Q 60/20 (2010.01)
(52) U.S. Cl. .............................. 850/31; 850/21; 850/30; 356/364; 356/367; 356/369; 356/497; 356/479; 356/491; 977/953

(58) Field of Classification Search ................... 850/21, 850/30, 31; 356/364, 367, 369, 497, 479, 356/491; 977/953; 250/306–311
See application file for complete search history.

(56) References Cited

U.S. PATENT DOCUMENTS 7,420,675 B2 * 9/2008 Giakos ....................... 356/364
(Continued)

FOREIGN PATENT DOCUMENTS

| WO | WO 2005/029015 A2 | 3/2005 |
| WO | WO 2007/130001 A2 | 11/2007 |

OTHER PUBLICATIONS

Silva, T.J., et al., "Scanning Near-Field Optical Microscope for the Imaging of Magnetic Domains in Optically Opaque . . . ", Applied Physics Letters, 65, 1994, No. 6, 658-660.

(Continued)

*Primary Examiner*—Jack I Berman
*Assistant Examiner*—Meenakshi S Sahu
(74) *Attorney, Agent, or Firm*—Joseph J. Crimaldi; Roetzel & Andress

(57) ABSTRACT

The present invention relates to near-field scanning optical microscopy (NSOM) and near-field/far-field scanning microscopy methods, systems and devices that permit the imaging of biological samples, including biological samples or structures that are smaller than the wavelength of light. In one embodiment, the present invention permits the production of multi-spectral, polarimetric, near-field microscopy systems that can achieve a spatial resolution of less than 100 nanometers. In another embodiment, the present invention permits the production of a multifunctional, multi-spectral, polarimetric, near-field/far-field microscopy that can achieve enhanced sub-surface and in-depth imaging of biological samples. In still another embodiment, the present invention relates to the use of polar molecules as new optical contrast agents for imaging applications (e.g., cancer detection).

26 Claims, 6 Drawing Sheets

U.S. PATENT DOCUMENTS

| | | | |
|---|---|---|---|
| 7,428,050 B2 * | 9/2008 | Giakos | 356/369 |
| 2005/0264813 A1 | 12/2005 | Giakos | |
| 2010/0133488 A1 * | 6/2010 | Giakos | 252/582 |

OTHER PUBLICATIONS

Hettich, C., et al., "Single Molecules, Single Nanoparticles and Their Opitcal Interaction", AIP Conference Proceedings, AIP USA No. 696, 2003, 127-135.

Giakos, G. C., "Novel molecular imaging and nanophotonics detection principles and systems", Imaging Systems and Techniques, 2005, 103-108.

* cited by examiner

Time scale

MOLECULAR IMAGING AND NANOPHOTONICS IMAGING AND DETECTION PRINCIPLES AND SYSTEMS, AND CONTRAST AGENTS, MEDIA MAKERS AND BIOMARKERS, AND MECHANISMS FOR SUCH CONTRAST AGENTS

FIELD OF THE INVENTION

The present invention relates to near-field scanning optical microscopy (NSOM) and near-field/far-field scanning microscopy methods, systems and devices that permit the imaging of biological samples, including biological samples or structures that are smaller than the wavelength of light. In one embodiment, the present invention permits the production of multi-spectral, polarimetric, near-field microscopy systems that can achieve a spatial resolution of less than 100 nanometers. In another embodiment, the present invention permits the production of a multifunctional, multi-spectral, polarimetric, near-field/far-field microscopy that can achieve enhanced sub-surface and in-depth imaging of biological samples. In still another embodiment, the present invention relates to the use of polar molecules as new optical contrast agents for imaging applications (e.g., cancer detection).

BACKGROUND OF THE INVENTION

Within the next decade, cancer will replace heart disease as the leading cause of death, according to National Cancer Institutes and the Centers for Disease Control and Prevention. Early diagnosis of cancer is of paramount significance to prognosis, staging, and treatment selection. Conventional imaging techniques, even when computer-assisted, typically produce images attributed to the anatomy and structure of the tumor and surrounding tissue, instead of the physiology and pathology of the tumor itself. As a result, classical imaging techniques are less than ideal tools for cancer diagnosis and assessment.

Optical imaging provides a detailed description of biological tissues. For instance, it allows the characterization of a variety of diseases, such as breast cancer, skin cancer, lung cancer, cancer of the bladder, and the analysis of molecular pathways leading to diseases. Functional imaging and molecular imaging have been introduced to describe new imaging paradigms. Specifically, functional imaging refers to the capability of non-invasively monitoring physiological processes, primarily based on blood flow and cellular metabolism. On the other hand, molecular imaging is a subset of functional imaging, which refers to imaging specifically targeted processes and pathways in cells and tissues.

More sensitive and specific optical imaging techniques, at the molecular level, that are capable of providing both metabolic and physiological information, could play an important role in the diagnosis and treatment of cancer. Better imaging could permit/allow for better diagnostic and therapeutic solutions to be applied selectively to the tumor, and could be used to better facilitate localized surgical interventions, such as detection of margins, ablation, endoscopy, and lumpectomy, that allow limited diseased areas to be treated more drastically. Better imaging could also facilitate minimally invasive monitoring of therapeutic response. Thus, the development of high specificity and high sensitivity optical imaging technologies would assist oncologists in developing gene-to-gene receptor-specific therapies, earlier cancer diagnosing, choosing stage-specific treatment options, and accurate assessment and follow-up. Therefore, priority should be given to the development of imaging technologies with enhanced specificity and sensitivity, capable of identifying the presence of cancer, as well as the stage, distribution, and type of cancer.

Accordingly, there is a need in the art for improved imaging techniques that can be used for, among other things, the diagnosis and treatment of diseases such as cancer.

SUMMARY OF THE INVENTION

The present invention relates to near-field scanning optical microscopy (NSOM) and near-field/far-field scanning microscopy methods, systems and devices that permit the imaging of biological samples, including biological samples or structures that are smaller than the wavelength of light. In one embodiment, the present invention permits the production of multi-spectral, polarimetric, near-field microscopy systems that can achieve a spatial resolution of less than 100 nanometers. In another embodiment, the present invention permits the production of a multifunctional, multi-spectral, polarimetric, near-field/far-field microscopy that can achieve enhanced sub-surface and in-depth imaging of biological samples. In still another embodiment, the present invention relates to the use of polar molecules as new optical contrast agents for imaging applications (e.g., cancer detection).

In one embodiment, the present invention relates to a multi-energy microscopy system comprising: (a) at least one energy source for irradiating a target and/or sample with at least one quantity of light and at least one quantity of energy, the at least one quantity of light comprising at least one wavelength of light and the at least one quantity of energy comprising at least one wavelength of energy, wherein the wavelength of the energy is either shorter or longer than the wavelength of the at least one quantity of light; (b) a polarization-state generator for generating a polarization state for each quantity of light, the polarization-state generator comprising at least one polarizer, each polarizer being adapted to polarize an individual wavelength before the one or more quantities of light enter a first waveplate; (c) a polarization-state receiver for evaluating a resulting polarization state of each of the one or more quantities of light following illumination of the target and/or sample, the polarization-state receiver comprising a second waveplate through which the one or more quantities of light are transmitted before entering at least one second polarizer; (d) an image-capture device for capturing at least a first image and a second image of the target and/or sample irradiated by the at least one quantity of light and the at least one quantity of energy, the first image corresponding to an image of the target and/or sample generated from the wavelength of light and the second image corresponding to an image of the target and/or sample generated from the wavelength of energy; (e) at least one near-field optics device; (f) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (g) a processing unit for assigning a weighting factor to at least one of the first and second images and evaluating a weighted difference between the first and second images to generate a multi-wavelength image of the target and/or sample, wherein the microscopy system utilizes/implements Stark-effect imaging.

In another embodiment, the present invention relates to a multi-energy near-field microscopy system comprising: (i) at least two different light sources for illuminating a target and/or sample under two photon and three-photon absorption-induced up-converted fluorescence; (ii) a polarization-state generator for generating a polarization state in the light generated by the at least two light sources; (iii) an image-capture device for capturing at least a first image and a second image of the target and/or sample illuminated by the at least two different light sources; (iv) at least one near-field optics device; (v) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (vi) a processing unit for assigning a weighting factor to at least one of the first and second images and evaluating a weighted difference between the first and second images to generate a multi-wavelength image of the target and/or sample, wherein the microscopy system utilizes near-field optics and implements Stark-effect imaging.

In still another embodiment, the present invention relates to a multi-energy far-field microscopy system comprising: (i) at least one light source for illuminating a target and/or sample with at least one quantity of light, the at least one quantity of light comprising at least two wavelengths of light, a first wavelength and a second wavelength, the second wavelength being different than the first wavelength; (ii) a polarization-state generator for generating a polarization state for each quantity of light, the polarization-state generator comprising at least one polarizer, each polarizer being adapted to polarize an individual wavelength before the one or more quantities of light enter at least one first waveplate; (iii) a polarization-state receiver for evaluating a resulting polarization state of each of the one or more quantities of light following illumination of the target and/or sample, the polarization-state receiver comprising at least one second waveplate through which the one or more quantities of light are transmitted before entering at least one second polarizer; (iv) an image-capture device for capturing at least a first image and a second image of the target and/or sample illuminated by the at least one quantity of light, the first image corresponding to an image of the target and/or sample generated from the first wavelength component of the at least one quantity of light and the second image corresponding to an image of the target and/or sample generated from the second wavelength component of the at least one quantity of light; (v) at least one near-field optics device; (vi) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (vii) a processing unit for assigning a weighting factor to at least one of the first and second images and evaluating a weighted difference between the first and second images to generate a multi-wavelength image of the target and/or sample.

In still another embodiment, the present invention relates to a multi-energy near-field microscopy system comprising: (A) at least one light source for illuminating a target and/or sample with at least one quantity of light, the at least one quantity of light comprising at least two wavelengths of light, a first wavelength and a second wavelength, the second wavelength being different than the first wavelength; (B) a polarization-state generator for generating a polarization state for each quantity of light, the polarization-state generator comprising at least one polarizer, each polarizer being adapted to polarize an individual wavelength before the one or more quantities of light enter through at least one rotating one-quarter (¼) waveplate linear retarder; (C) a polarization-state receiver for evaluating a resulting polarization state of each of the one or more quantities of light following illumination of the target and/or sample, the polarization-state receiver comprising at least one second rotating one-quarter (¼) waveplate linear retarder through which the one or more wavelengths of light are transmitted before entering at least one second polarizer; (D) an image-capture device for capturing at least a first image and a second image of the target and/or sample illuminated by the at least one quantity of light, the first image corresponding to an image of the target and/or sample generated from the first wavelength of light and the second image corresponding to an image of the target and/or sample generated from the second wavelength of light, wherein the image-capture device receives and/or generates for each of the at least first and second images at least 16 individual polarization-state measurements; (E) at least one near-field optics device; (F) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (G) a processing unit for comparing the at least 16 individual polarization state measurements from the at least first and second images, wherein the microscopy system utilizes near-field optics and implements Stark-effect imaging.

In still another embodiment, the present invention relates to a method for generating a multi-modality image of a target and/or sample, the method comprising the steps of: (i) emitting at least two quantities of energy, at least one quantity of energy being a quantity of light having a first wavelength, the second quantity of energy having a second wavelength that is either longer of shorter than the first wavelength of light; (ii) creating an initial polarization state for at least the one quantity of light by polarizing and then retarding one component of the at least the one quantity of light relative to another component of the at least one quantity of light; (iii) directing the at least two quantities of energy generally toward the target and/or sample so that the target and/or sample is irradiated by the at least two quantities of energy, including directing the polarization state of any polarized energy generally toward the target and/or sample in the instance where at least a portion of the energy is polarized; (iv) analyzing a resulting polarization state for each of the first and second quantities of energy by retarding one component of the first and second quantities of energy following irradiation of the target and/or sample relative to another component of the first and second quantities of energy, and then polarizing the retarded first and second quantities of energy; (v) capturing a first image of the target and/or sample irradiated by the first quantity of energy and a second image of the target and/or sample irradiated by the second quantity of energy; (vi) optionally weighting at least one of the first and second images; and (vii) generating the multi-energy image of the target and/or sample by evaluating a weighted difference between the first and second images, and/or by comparing and/or combining the first and second images.

DETAILED DESCRIPTION OF THE INVENTION

Figure 1:
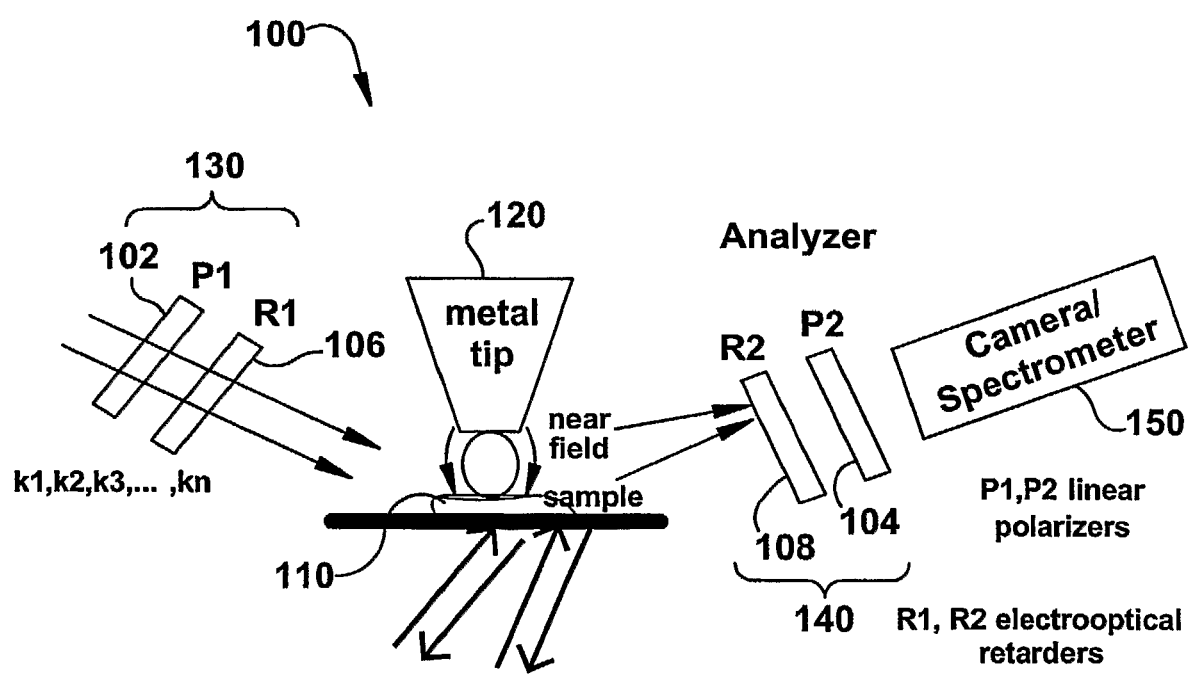
FIG. 1 is a multi-spectral Mueller matrix/Stokes parameter apertureless near-field scanning microscopy system according to one embodiment of the present invention.

The present invention relates to near-field scanning optical microscopy (NSOM) and near-field/far-field scanning microscopy methods, systems and devices that permit the imaging of biological samples, including biological samples or structures that are smaller than the wavelength of light. In one embodiment, the present invention permits the production of multi-spectral, polarimetric, near-field microscopy systems that can achieve a spatial resolution of less than 100 nanometers. In another embodiment, the present invention permits the production of a multifunctional, multi-spectral, polarimetric, near-field/far-field microscopy that can achieve enhanced sub-surface and in-depth imaging of biological samples. In still another embodiment, the present invention relates to the use of polar molecules as new optical contrast agents for imaging applications (e.g., cancer detection).

In one embodiment, the present invention relates to a near-field scanning optical microscopy (NSOM) and/or near-field scanning microscopy (NSM) system that utilizes, in part, a multi-energy system that generates and/or forms images of targets/structures by applying Mueller matrix imaging principles and/or Stokes polarimetric parameter imaging principles to data obtained by the multi-energy system. In one embodiment, the present invention utilizes at least one energy or light source to generate two or more Mueller matrix and/or Stokes polarization parameters images of a target/structure, and evaluates the Mueller matrix/Stokes polarization parameters multi-spectral difference(s) between the two or more images of the target, sample and/or structure. As a result, high contrast, high specificity images can be obtained. Additional information can be obtained by and/or from the present invention through the application of image, Mueller matrix decomposition, and/or image reconstruction techniques that operate directly on the Mueller matrix and/or Stokes polarization parameters.

The present invention also relates to optical imaging techniques for efficient detection, characterization, and/or interrogation of targets/samples. High-contrast multi-spectral Mueller matrix/Stokes parameters polarimetric difference images, and the like can be obtained from targets that are, for example, within an organism or other medium. As such, although not limited strictly thereto, the present invention is particularly suited to use in medical and/or biological applications.

The principles of multi-spectral Mueller matrix-polarimetric image difference of this invention comprise multiple optical Mueller polarimetric images, obtained at different wavelengths. A weighted subtraction of any high-energy Mueller matrix image (low wavelength) image from a low energy (high wavelength) Mueller matrix image produces a polarimetric Mueller matrix image difference. Further imaging information of the target, sample and/or structure can be obtained by applying Mueller matrix polar decomposition of images obtained at least two different wavelengths, thereby yielding image differences between at least one set of images obtained from a target/sample/structure at least two individual wavelengths. In fact, Mueller matrix measurement allows parameters such as diattenuation, retardance, depolarization power, and birefringence to be obtained. The importance of these parameters can be enhanced further under multi-spectral interrogation of the target and/or sample, providing useful information regarding the nature of the target and/or sample.

For instance, interrogation of biological structures with multiple wavelengths, leads in practice to a multilayer interrogation of tissue, allowing one to obtain high-contrast images at different depths. This permits/allows one to differentiate tumor and cancerous structures or cells from healthy ones based on a change in tissue birefringence. Therefore, a subtraction of the birefringence obtained at least two distinct wavelengths can enhance the structure of interest, removing the interfering tissue or cells. Therefore subtraction of the diattenuation, retardance, depolarization power, and birefringence at distinct wavelengths, under multi-spectral interrogation of a target can provide insightful structural and physiological information based on the difference of the attenuation of amplitude of incident light, phase change difference, depolarizing potential of the target and/or sample difference, and/or phase shift difference, due to the variation of index of refraction, obtained at least two distinct wavelengths, respectively. Therefore, multi-spectral interrogation of the target and/or sample, and formation of Mueller matrix-polarimetric image differences, can enhance just a specific region of interest (ROI) of the target and/or sample over another ROI.

Further image enhancement can be achieved, by means of Stokes parameters formalism, by forming polarimetric images differences and the like, such as degree of polarization (DOP) difference, degree of linear polarization (DOLP) difference, degree of circular polarization (DOCP) difference, obtained at different wavelengths. This methodology can increase by n-fold the signal-to-noise ratio of the imaging targets.

The present invention can utilize a laser beam, or other light source or sources, in conjunction with suitable optical filters and components, to illuminate targets, samples, structures and/or scenes at specific wavelengths and interrogate their respective reflectance spectral features. The dual-phase rotating retarder polarimeter yields a complete measurement of all sixteen Mueller matrix elements. As a result, complete polarimetric signatures of the targets and/or samples are obtained. The acquisition of Mueller-matrix/Stokes parameters polarimetric optical images, one produced from a high energy (small wavelength) and another from a low energy (large wavelength) laser beams, and the subsequent subtraction of these two images, can produce high-contrast polarimetric image difference which eliminates or minimizes interfering background and clutters, or enhances the image process, meanwhile provide, spectral, energy, polarization-based amplitude contrast and phase contrast information, enhanced ROI's, enhanced contrast, enhanced specificity, and high signal-to-noise ratio. The detected signal can be further enhanced by embedding fluorescent particles or molecules, quantum dots, nanostructures, dopants, polar molecules, chemoluminescence and bioluminescence particles or molecules, into the target, sample and/or background.

The present invention operates on multi-spectral, multi-fusion, multifunctional, Muller matrix polarimetric principles. It is capable of interrogating targets or samples with multiple wavelengths forming multi-spectral Mueller matrix multi-wavelength polarimetric difference images. Multi-spectral target interrogation gives rise to multi-wavelength Muller matrix polarimetric image differences obtained at different wavelengths, which also contain energy, spectral, polarization-based amplitude contrast and phase contrast information simultaneously. These principles apply not only to the interrogation of multiple targets but also single targets as well, giving rise to enhanced spectral and polarimetric contrast data.

In one embodiment, the design principles of the present invention's near-field scanning microscopy (NSM) and/or near-field scanning optical microscopy (NSOM) are shown in FIG. 1. In FIG. 1, apertureless near-field optics 120 are coupled to a Mueller matrix/Stokes parameter polarimeter as shown, with P1 representing a first linear polarizer 102, R1 representing a first retarder 106, R2 representing a second retarder 108, and P2 representing a second linear polarizer 104.

More specifically, in this embodiment the present invention permits the production of a near-filed microscopy system/device that can achieve a spatial resolution of less than 100 nm. Such a resolution is significantly better than that allowed by the diffraction limit. An imaging device according to one embodiment of the present invention is illustrated in FIG. 1. As is shown in FIG. 1, an imaging system 100 according to one embodiment of the present invention comprises linear polarizers 102 and 104, electro-optical retarders 106 and 108, near-field optics 120, and an optical image-capture device 122 (e.g., a camera or spectrometer). System 100 of the present invention can be operated as a Mueller matrix polarimeter or as a Stokes parameter polarimeter depending upon the choice and operation of the components contained therein.

Also included in system 100, although not pictured, are a light source (e.g., a multi-spectral light source) for illuminating a sample 110 with a first quantity of light having at least a first wavelength and a second wavelength of light. Alternatively, the present invention can utilize a light source for illuminating sample 110 with a first quantity of light having at least a first wavelength and a second quantity of light having a second wavelength. However, the present invention is not limited to just the above embodiments. Rather, the present invention can utilize one or more quantities of light, each quantity of light being composed of at least one specific wavelength of light and/or energy, or even two or more specific wavelengths of light and/or energy.

Although described herein as a dual-energy imaging system, it should be understood that the system 100 of the present invention can be used to generate and display any multi-energy image. Instead of being limited to two quantities of light, a plurality of light quantities, described interchangeably herein as beams of light, laser light beams, and laser beams, each having a different wavelength, are used to illuminate and/or irradiate sample 110 for capturing images of sample 110. Alternatively, the present invention can also utilize at least one quantity of light, where the light quantity simultaneously or discretely contains therein at least two different wavelengths of light.

In another embodiment, the present invention can optionally utilize a quantity of light having a first wavelength and another quantity of energy having a second wavelength, the quantity of energy having a wavelength that is either longer or shorter than the wavelength of light.

Regardless of the number of different wavelengths used for illumination purposes, the principles of multiple-energy imaging involve the use of two or more images to generate a multi-energy image. In a two wavelength embodiment of the present invention, a first image is captured by illuminating sample 110 with light having the first wavelength, and at least one more image is captured by illuminating sample 110 with light or some other energy source having a second wavelength that is different than the first wavelength. Optionally, this can be performed with a quantity of light having a first wavelength and another quantity of energy or light having a second wavelength that is either longer or shorter than the wavelength of the light.

The terms long and short as used with reference to the wavelengths of light and/or energy used to illuminate/irradiate sample 110 are relative terms that are ordinarily open to subjective interpretation. As used herein, however, the terms long and short are relative to common electromagnetic spectrum known to those of skill in the art.

As is shown in FIG. 1, linear polarizer 102 and electro-optical retarder 106 together form a polarization-state generator 130. Polarization-state generator 130 is designed to generate a polarization state for each quantity of light that passes there through. Through the use of the linear polarizer 102 of polarization-state generator 130, through which the first and second wavelengths of light are transmitted before entering a first waveplate 32 (e.g., a one-quarter waveplate), a phase difference between an ordinary component and an extraordinary component 42 of the polarized first and second wavelengths of light is created. A polarization-state receiver 140 is positioned to evaluate a resulting polarization state of the first and second wavelengths of light following illumination of sample 110, the polarization-state receiver 140 including a second electro-optical retarder 108 (e.g., a one-quarter waveplate) through which the first and second wavelengths of light are transmitted before entering a second linear polarizer 104. The polarization-state receiver can be just a receiver or it can be both a receiver and a polarization-state analyzer, if so desired.

An optical image-capture device 150, such as a charge-coupled device ("CCD"), photo-electronic camera, CMOS detector, a photomultiplier, an intensified camera, homodyne/heterodyne, auto-balanced detectors, or the like captures a first image of the target and/or sample illuminated by the first wavelength of light and a second image of the target and/or sample illuminated by the second wavelength of light. A processing unit (not shown) assigns a weighting factor to at least one of the first and second images and evaluates a weighted difference between the first and second images to generate a multi-energy image (or polarimetric image) of sample 110. For instance, where both waveplates are one-quarter retarders and whether both one-quarter retarders rotate, or just the second one-quarter retarder rotates, under suitable orientation of the optical components, the system of the present invention forms a dual-phase rotating retarder complete Mueller matrix polarimeter, or a rotating retarder Stokes parameters polarimeter. Alternatively, a polarimetric system with no moving parts can be established by using electro-optical retarders on both the transmitter and receiver sides.

In one embodiment, the processing unit can process at least 16 individual polarization-state measurements received/derived from the images generated from the first and second wavelengths of light. These values, can be averaged together to form average polarimetric images at distinct wavelengths. Then, the first average polarimetric image corresponding to an image of the target and/or sample generated from the first wavelength of light and the second average polarimetric image corresponding to an image of the target and/or sample generated from the second wavelength of light, are subtracted to each other so that to obtain a weighted spectral image difference of the target and/or sample. Alternatively, or in addition to, the processing unit can process at least 16 individual polarization-state measurements.

In one embodiment, the present invention also includes a common computational platform, not shown in FIG. 1, that is designed to store information concerning the wavelengths of the light emitted by each individual imaging system 100 in a database stored in a computer readable memory for optimizing operation of the network in future applications. An artificial neural network ("ANN"), described in detail below, can be used in conjunction with the computational platform to select optimal wavelengths for the individual light source(s) used in system 100. The optimal wavelengths can depend on a variety of factors such as propagation medium, the properties of sample 110 (i.e., whether the sample of interest includes biological tissue, bone structures, gaseous areas or portions, hardened structures or implants, synthetic objects or implants, etc.), and other factors.

The necessary computational hardware and software for the operation of the system 100 of the present invention is in operational communication with the features of the system 100 discussed above. The computational platform includes at least a processing unit operatively connected to a computer readable memory. Programmable arrays or signal processors stored in the computer-readable memory along with information collected from previous operations of the system 100 and pre-programmed into the computer readable memory allow the system 100 to adaptively select suitable wavelengths for the first and second quantities of light based on at least the ambient environment of sample 110. For example, the computational platform can include what is commonly referred to as an intelligent system, such as an artificial neural network, to determine the optimal wavelengths to be used for a desired and/or given application. Alternatively, a database of information can be preprogrammed into the computer-readable memory to minimize the time required for the learning process.

In one embodiment, the present invention utilizes an ANN of the present invention uses a committee of neural networks to increase the reliability of choices made by the ANN. Three or more ANNs are trained with different architecture, initial weights, and the best ANNs are recruited to form a committee for selecting the appropriate light wavelengths. Inexact-reasoning techniques such as fuzzy logic can be employed to further enhance the system.

In use the system of FIG. 1 operates as follows, system 100 of the present invention can generate enhanced multi-energy images according to a method of the illustrative embodiment. This illustrative method includes the steps of emitting a first quantity of light having a first wavelength and a second quantity of light having a second wavelength that is different than the first wavelength, creating an initial polarization state for each of the first and second quantities of light by polarizing and then retarding one component of each of the first and second polarized quantities of light relative to another component of the first and second quantities of light, and directing the polarization state for each of the first and second quantities of light generally toward a sample or target. The method of the illustrative embodiment further includes analyzing a resulting polarization state for each of the first and second quantities of light by retarding one component of the first and second quantities of light following illumination of sample 110 relative to another component of the first and second quantities of light, and then polarizing the retarded first and second quantities of light; capturing a first image of sample 110 illuminated by the first quantity of light and a second image of sample 110 illuminated by the second quantity of light; weighting at least one of the first and second images; and generating the multi-energy image of the target and/or sample by evaluating a weighted difference between the first and second images. The weighting factor in some circumstances can be unity, or take on any other value.

The step of creating an initial polarization state includes linearly polarizing the first and second quantities of light. After the linear polarization, at least one of the ordinary and extraordinary components of the linearly-polarized light is retarded with, for example, a quarter-wave retarder to create a phase angle between the ordinary and extraordinary components.

Similarly, analyzing the resulting polarization state includes analyzing a resulting phase angle between the ordinary and extraordinary components of the first and second quantities of light following interaction of the first and second quantities of light with sample 110. This step evaluates the effect sample 110 has on the polarization state of the first and second quantities of light by transmitting the first and second quantities of light through a second quarter-wave retarder following interaction with the target and/or sample. Then, the first and second quantities of light are again linearly polarized by the second polarizer.

Next, a Mueller matrix for each of the first and second images, acquired at two different wavelengths, are determined. Then, a Muller matrix difference is generated from the difference between the two Muller matrix images, and an image representing the Muller matrix difference is displayed.

In one embodiment, emitting a first quantity of light having a first wavelength and a second quantity of light having a second wavelength may optionally include evaluating an ambient environment of sample 110, comparing the ambient environment of sample 110 to known conditions stored in a computer readable memory, and determining suitable first and second wavelengths based on the comparison between the evaluated ambient environment of sample 110 and the known environments in the computer readable memory using an artificial fuzzy neural network. The ambient environment can be any environment, neighboring object, and the like that can affect the first and second quantities of light en route to sample 110.

A further discussion of other suitable imaging systems that can be used in combination with near-field optics 120 are discussed in U.S. patent application Ser. No. 11/129,769, which is hereby incorporated by reference in its entirety. Also of interest is the discussion contained in PCT Application No. PCT/US06/11059, filed Mar. 28, 2006, the disclosure of which is hereby incorporated by reference in its entirety.

In still another embodiment, the imaging system 100 of the present invention fuses dual-energy imaging principles with polarimetric imaging principles, optionally at varying focal depths and exposures, to generate and display a high-contrast image. The interrogation of a sample 110 with two or more quantities of light having different wavelengths (multi-spectral interrogation), and the acquisition of polarimetric images by applying dual-rotating quarter-wave linear-retarder complete-polarimeter techniques, allows one to obtain enhanced polarimetric signatures by subtraction of the polarization parameters of the acquired images, such as degree of polarization (DOP), degree of linear polarization (DOLP), degree of circular polarization (DOCP), ellipticity, azimuth, and eccentricity, or their differences such as DOP difference, DOLP, difference, DOCP difference, obtained at different wavelengths.

In one instance, in the embodiment depicted in FIG. 1, a weighted subtraction of the two images produces a multi-energy image which minimizes interfering background structures. A weighting factor is assigned to at least one polarization parameter of one or more of the captured images such that the desired contrast is achieved in the multi-energy image generated by evaluating a difference between the images of sample 110 illuminated with the quantities of light having different wavelengths.

Multi-energy images of the present invention can be one dimensional, two dimensional, and three dimensional. Further, the optical image-capture device 150 can rely on homodyne, heterodyne, superheterodyne detection principles, image intensifiers, photomultipliers, semiconductor detectors, including but not limited to the use of auto balanced detectors and lock-in amplifiers.

Examples of the polarization parameters of the captured images that can be weighted for subtraction from the corresponding polarization parameters of another image captured by illuminating the target and/or sample 110 at a different wavelength include, but are not limited to: degree of polarization ("DOP"), degree of linear polarization ("DOLP"), degree of circular polarization ("DOCP"), ellipticity, azimuth, and eccentricity. The weighted subtraction can also be performed using sets of images, in which case the subtraction will performed on the differences of the sets such as DOP difference, DOLP difference, DOCP difference, ellipticity difference, azimuth difference, eccentricity difference and the like.

As noted above, near-field scanning optical microscopy allows one to probe imaging of biological samples, smaller than the wavelength of light. As a result, it can be achieved a spatial resolution of less than 100 nm, significantly better than that allowed by the diffraction limit. The design principles of the present invention are shown in the embodiments illustrated in FIGS. 1, 2(a) and 2(b), in these embodiments apertureless near field optics, operating at multiple wavelengths are coupled to a Mueller matrix/Stokes parameter imaging polarimeter as well as to a spectro-polarimeter. In light of this, the present invention is capable of providing spatial, spectral, and temporal resolution, with enhanced polarization discrimination capabilities. A combination of laser sources, a laser source with a number of lasing lines, a tunable light source over a broad range, or LED's can be used as the light source for the embodiments of FIGS. 1, 2(a) and 2(b). An achromatic objective lens capable to focus different excitation wavelengths at the same spot could also be utilized in the embodiments of FIGS. 1 and 2(b).

The above principles apply towards the design of aperture-controlled near-field scanning microscopes (NSM), and aperture-controlled near-field scanning optical microscopes (NSOM), by using polarimetric preserved fibers or polarizing fibers or a combination of the two.

Such devices can provide enhanced imaging and spectral polarimetric information regarding the metabolic information of a tissue, as well as the molecular mechanism of a biological function, drug-cell interaction, single-molecule imaging, and so on.

In another embodiment, the systems/devices of the present invention can also be operated in a fluorescence mode, providing spatial distribution of the fluorescence intensity and enhanced imaging and detection capabilities. In still another embodiment, the present invention could interrogate samples using laser beams, LEDs, polychromatic light sources, combinations of two or more thereof, or a combination of active-passive light sources. In yet another embodiment, the present invention could be used to obtain high contrast Mueller matrix polarimetric images and/or Stokes polarization parameters images, or Mueller matrix polarimetric spectral image differences (dual-energy subtraction), and/or Stokes polarization parameters spectral image differences (dual-energy subtraction).

The present invention can operate alone, or in conjunction with, an atomic force microscope, macroscopic imaging system, confocal microscope, optical tomography, Raman microscopy, non-linear optical imaging, fluorescence lifetime imaging, and/or any other microscopy system and/or spectro-polarimetric system. The present invention could also operate in conjunction with any kind of polar molecule contrast agents and/or polar biomarkers (e.g., gaseous, liquids, solid, organic, inorganic, biological, biochemical, physiological solutions, polymers, etc.) leading to enhanced detection and imaging of the target and/or sample, as well with quantum dots, spectral fluorophores, and/or nanoparticles/nanostructures.

When used in conjunction with polar molecular structures, or metallic nanostructures, a device/system according to the present invention could also enhance the fluorescence yield, due to the local electric field enhancement, yielding enhanced images of a structure. The above design concepts, as they relate to near-field/far-field scanning microscopy applies to the development of imaging technologies having high resolution, high contrast, and/or high specificity, systems for both thin and thick samples. Devices/systems in accordance with the present invention can be also combined with other signal descriptors (temporal, frequency, spatial, etc.), and multimodalities such as any combination of optical/fluorescent radiation/quantum radiation/electromagnetic radiation/ultrasound.

An enhanced version of a near-field microscopy system according to the present invention would be implemented with Stark-effect imaging capabilities, in addition to the above, by applying an electric field on the tip (DC field would be one possible solution) so that with the applied light field, and the use of polar molecules/metallic nanostructure, such a device/system would yield high contrast and/or high resolution images.

Devices/systems in accordance with the present invention have a wide variety of possible applications. Some exemplary applications include, but are not limited to, medical imaging, cancer detection, tumor detection, assessment of disease, follow-up medical imaging, margin detection, cellular imaging, physiological imaging, single molecule imaging, enhanced imaging systems, enhanced microscopy systems, molecular diagnostics and imaging, molecular analysis of a disease, drug development, proteomics, genetics, genomics, metabonomics, immunologic to expression profiling to imaging, pharmacogenomic markers predicting drug response and risk of adverse events, development of efficient sensors microfluidic micro/nanochips, LAB-on-a Chip, MEMS, nano- MEMS, analytical instrumentation, semiconductor inspection, material inspection, biology, biochemistry, biodefense, and industrial and/or military applications.

In addition the use of polar molecules and metallic nanostructures can be used for other applications, in conjunction with fluorescence, for enhanced underground, underwater detection of targets, mines, etc.

Figure 2A:
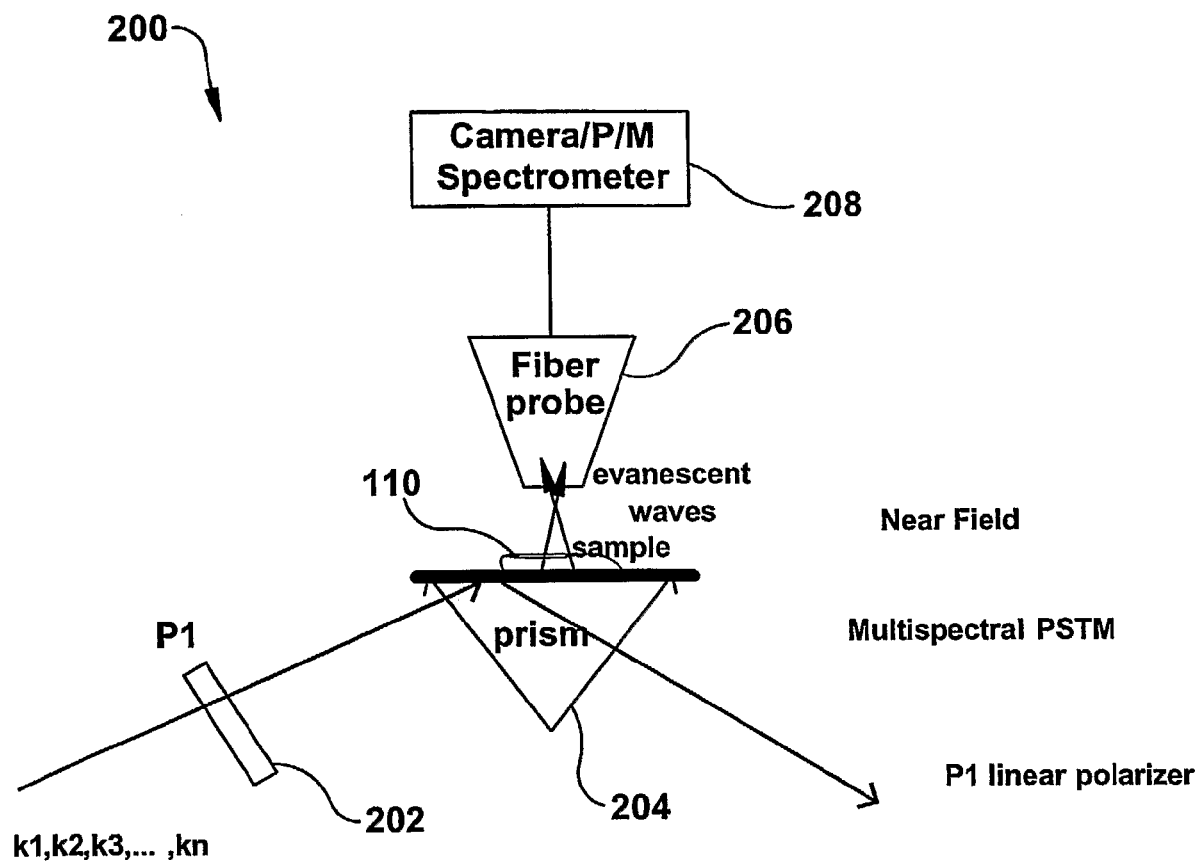
FIG. 2(a) is an illustration of a multifunctional, multi-spectral, imaging sensing design according to one embodiment of the present invention.

Specifically with regard to FIG. 2(a), in FIG. 2(a) a multifunctional, multi-spectral, imaging sensing system 200 is illustrated. System 200 of FIG. 2(a) includes a linear polarizer 202, a energy and/or light source (not shown), a prism 204, a sample 110, and a fiber probe 206 that is operatively coupled/connected to a camera/spectrometer 208. System 200 operates by varying the probe-sample distance in the near-field as a multi-spectral photon scanning tunneling microscope (PSTM) in which the sample is illuminated in a total internal reflection geometry using evanescent waves.

Figure 2B:
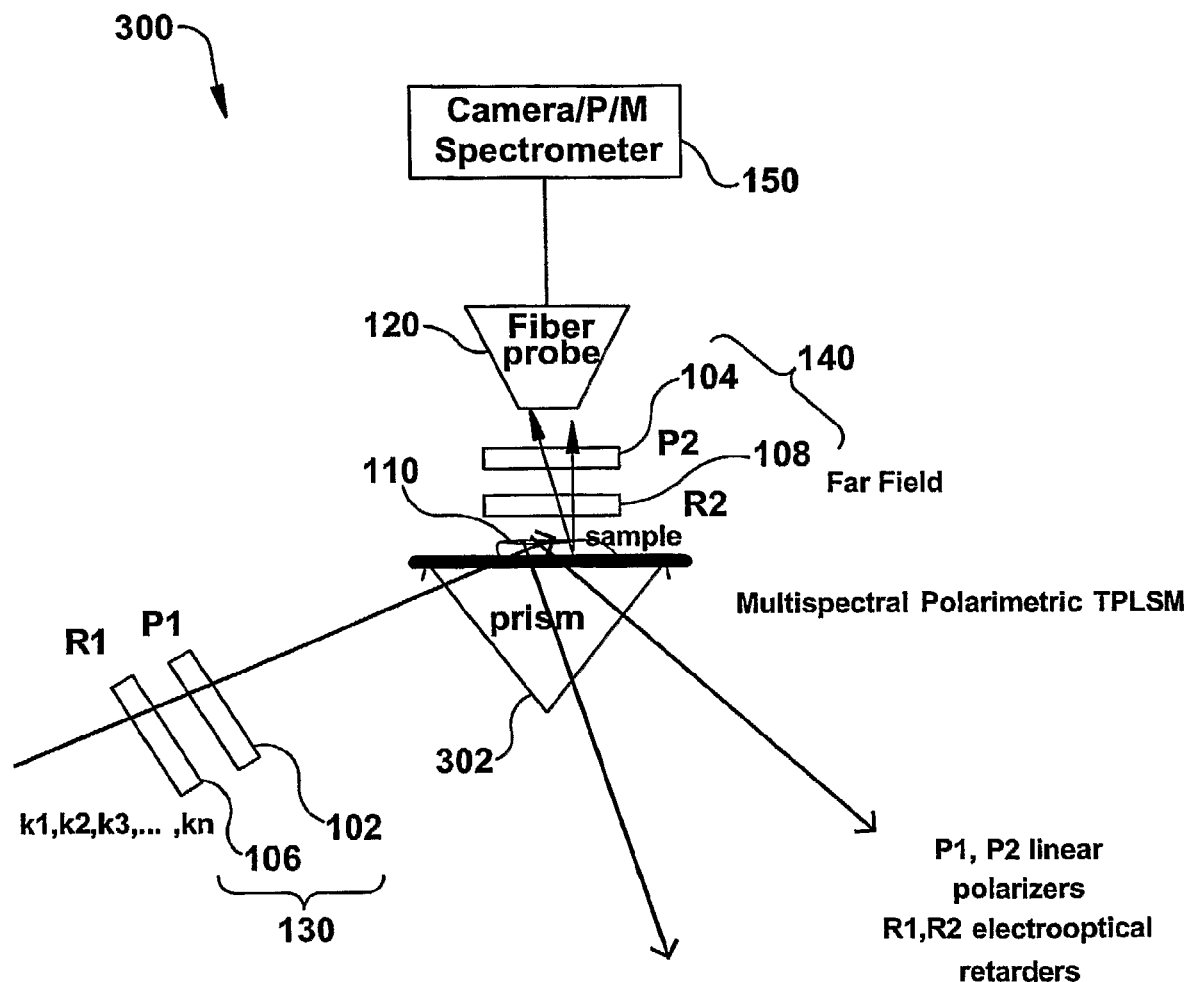
FIG. 2(b) is an illustration of another multifunctional, multi-spectral, imaging sensing design according to the present invention.

FIG. 2(b) illustrates another embodiment of a multifunctional, multi-spectral, imaging sensing system 300. The design of system 300 is similar in nature to that of system 100 of FIG. 1 except that system 300 includes a prism 302 and a fiber probe as its near-field optics 120. System 300 operates as a multi-photon, Mueller matrix/Stokes parameters far-field scanning microscopy system and can be utilized for bio-imaging applications. Thus, system 300 is a polarimetric, two-photon laser scanning microscopy system (TPLSM).

Figure 3:
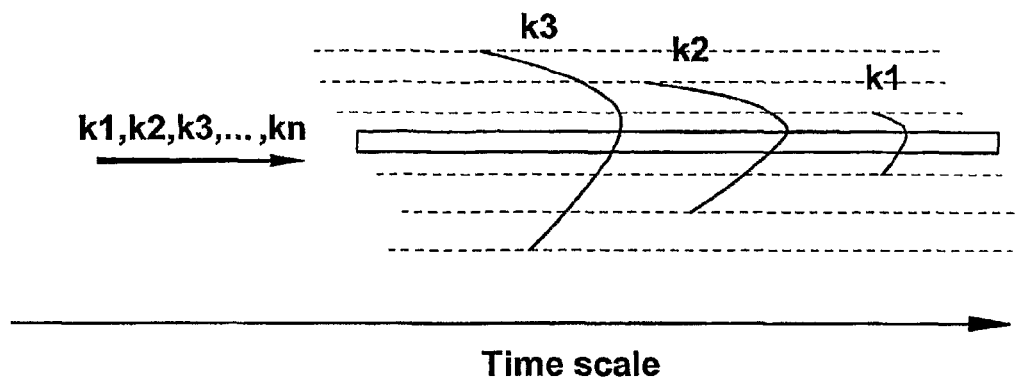
FIG. 3 is an illustration of the principles of a multi-spectral catheter/endoscope-like evanescent waves design, with enhanced sectioning capabilities, that permits the generation of different penetration depths illustrating interrogation planes into tissue, under conditions of total internal reflection.

The uniqueness of the system of FIG. 2(a) consists in the providing of precious information at very narrow slices of the tissue, at different penetration depths (typically, between 50-100 nm), according to:

$$d_{p,i} = \frac{\lambda_i}{2\pi n_1 \sqrt{\sin^2\theta - (n_2/n_1)^2}}$$

where the subscript i indicates the interrogation of the sample by multiple wavelengths $\lambda_1, \lambda_2, \ldots \lambda_n$. Therefore, enhanced structural and metabolic information, in the spatial, spectral, and temporal domain. In addition, a multifunctional imaging/detector system according to the present invention can be utilized to detect auto-fluorescence. Endogenous fluorophores are not uniform in tissue, therefore, the fluorescent spectrum emerging from different tissue layers is different. The fact, that auto-fluorescence differs among malignant and pre-malignant structures, with respect to the normal tissue, make this device suitable for early cancer detection, or a useful tool to the surgeon for detection of margins, during cancer operation. In order, to offer in vivo capabilities, these principles can be integrated into a catheter/endoscope-like design, by generating different penetration-depth into the tissue, a novel under conditions of total internal reflection (see FIG. 3). Depending upon the geometry used, planar or tomographic optical images can be generated. In addition, by subtracting slices obtained at two different wavelengths, (spectral difference), implemented with temporal difference (when possible) higher contrast, interfering structures can be removed, and enhanced contrast can be obtained.

Depending upon the geometry used, planar or tomographic optical images can be generated. In addition, by subtracting slices obtained at two different wavelengths, (spectral difference), implemented with temporal difference (when possible) higher contrast, interfering structures can be removed, and enhanced contrast can be obtained. Depending upon the application, the multi-spectral photon scanning tunneling microscope system of FIGS. 2(a) and/or 3, can be used as a standalone.

According to another embodiment of the present invention, a multi-photon, Mueller matrix/Stokes parameters far-field scanning microscopy system is shown in FIG. 2(b). The uniqueness of system 300 of FIG. 2(b) consists in providing precious imaging information from larger depths in a sample, without discernible "out-of-focus" fluorescence, and sectioning ability without using confocal microscopy. System 300 can be obtained by increasing the probe-sample distance in order to detect far-field light contributions. Typically, system 300 operates under-two photon and three-photon absorption-induced up-converted fluorescence. By utilizing a two-photon absorption-induced up-converted fluorescence for bio-imaging applications, a polarimetric two-photon laser scanning microscopy system (TPLSM) with enhanced imaging potential can be realized. Simultaneous multicolor imaging over the entire visible spectra is possible since the typically red and NIR wavelengths, deeper penetration than the UV, used as excitation sources give rise to fluorescence in the visible range.

An enhanced version of these systems would be implemented with Stark-effect capabilities, by applying a DC electric field on a suitably designed tip or probe architecture so that with an applied fast pulse lightwave field, and the use of polar molecules/metallic nanostructures, to yield to high contrast/high resolution images, when feasible.

Both the designs of FIGS. 1 and 2(b) could be utilized to obtain high contrast images through arithmetic manipulations of the acquired multi-spectral images, as well as through Mueller matrix polarimetric spectral image differences at different wavelengths (dual-energy subtraction), and/or Stokes polarization parameters spectral image differences (dual-energy subtraction). Again, temporal information can be combined to the spectral one to provide enhanced images.

In one embodiment, an imaging system in accordance with the present invention can provide enhanced imaging and spectral polarimetric information regarding the metabolic information of the tissue, as well as the molecular mechanism of a biological function, drug-cell interaction, single-molecule imaging, and so on. In another embodiment, an imaging system in accordance with the present invention can also be operated in the fluorescence mode, providing spatial distribution of the fluorescence intensity.

One issue in single molecule detection is to achieve a sufficient high signal-to-noise ratio so that the weak fluorescence from one individual molecule can be distinguished from the background. Similarly, to image the molecular features of cancer, it is necessary to deliver sufficient contrast agent to a tissue or tissues in order to achieve an adequate signal-to-noise ratio. The present invention achieves the aforementioned goal(s) via the use of near-field/far field microscopy. Quantum dots, up-converting nanophosphors, encapsulated dyes, plasmonic nanostructures, dye-doped nanoparticles, and other compounds are promising optical contrast agents for bio-imaging, and bio-detection.

In one embodiment, the present invention relates to the use of polar molecules as contrast agents for optical imaging both at the macroscopic and microscopic level. In this regard, sample experiments with solutions containing different concentrations of polar molecules are performed. This line of reasoning is motivated by the fact that the high activity of tumor cells requires more glucose (polar) uptake than normal cells. Since, glucose is an optically active substance, it introduces a rotation of the transmitted light polarization. While not wishing to be bound to any one theory, the concentration of glucose in cells should be proportional to the progress of disease.

Another advantage of using polar molecules as contrast agents is that they could and/or should exhibit a coupling of their electric dipole with the optical field, leading to enhanced focusing characteristics due to pseudo Stark effects, local field enhancement, and other non-linear mechanisms. Coupling of the optical field with DC fields could/would lead to enhanced Stark effects and detection characteristics. Interestingly enough, polar contrast molecules in conjunction with spectral polarimetric techniques, fluorophores and optical nanostructures could significantly enhance the single-molecule detection process.

In another embodiment, the present invention relates to the use of polar molecules or aggregates, as markers, biomarkers, contrast agents for optical imaging both at the macroscopic and microscopic level. The use of polar molecule contrast agents can enhance the detection process of physiological mechanisms and structures, and could contribute to the early detection, assessment, and progress of tumors. Again, as an example, the high activity of tumor cells requires more glucose (a polar compound) uptake than normal cells. Since, as noted above, glucose is an optically active substance, it introduces a rotation of the transmitted light polarization. Again, while not wishing to be bound to any one theory, the concentration of glucose in cells should be proportional to the progress of disease.

The polar molecules contemplated by the present invention could be any suitable polar molecule that could be used as a contrast agent. In another embodiment, the polar molecules can also bind to other targets such as nanoparticles/nanostructures, tumors, antigens, fluorophores, quantum dots, proteins, amino acids, forming more complex polar molecular structures with distinct/high specificity, marking/contrast features.

The above concepts applies to the development of high resolution/high contrast/high specificity of imaging technologies, systems and detection techniques both macroscopic or microscopic, or combination of them, as well as in combination with other signal descriptors, optical/fluorescent radiation/quantum radiation/electromagnetic radiation/ultrasound. Also they apply for the development of high contrast/high specificity sensors, biosensors, MEMS/nano-MEMS, nanostructures or nano-robots operating on single or multi-modality detection principles. In addition, all aspects of the present invention, including the contrast agents, apply not only for medical/biological imaging, detection assessment and follow-up of diseases, but also to other industrial, civilian, and military applications.

Figure 4:
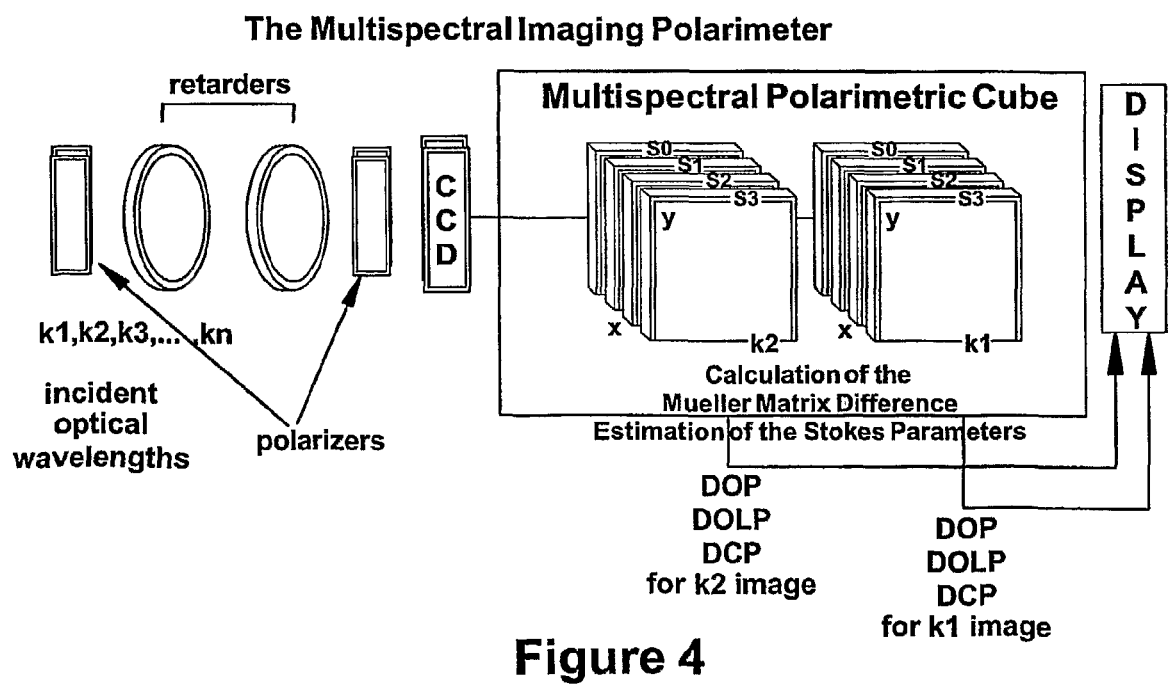
FIG. 4 is a diagram representing one example of a multi-spectral imaging polarimeter according to one embodiment of the present invention.

Polarimetric Formalism:

The principles of the multi-fusion multi-spectral-dual-rotating retarder, dual-energy complete polarimeter are discussed below and in FIG. 4. However, the present invention can be applied to any theoretical or experimental technique that estimates at least the full 16 element Mueller matrix of a system (target/associated optics), and relates, therefore, the output Stokes parameters to the input Stokes parameters.

(a) Mueller Matrix Spectral Difference:

The data from both the multi-spectral imaging camera can be interpreted as an image of a four-dimensional multi-spectro-polarimetric volume because a measure of radiance is obtained for four independent variables or indices: two spatial variables (x, y), a wavenumber k (or a wavelength) and S which has only four possible values ($S_0$, $S_1$, $S_2$, $S_3$).

Interrogation of the sample at multiple wavelengths yields several Mueller Matrices, expressed as:

$$M_{(sample)\lambda_1,\lambda_2,\ldots,\lambda_n} = \begin{pmatrix} m_{11\lambda_1,\lambda_2,\ldots,\lambda_n} & m_{12\lambda_1,\lambda_2,\ldots,\lambda_n} & m_{13\lambda_1,\lambda_2,\ldots,\lambda_n} & m_{14\lambda_1,\lambda_2,\ldots,\lambda_n} \\ m_{21\lambda_1,\lambda_2,\ldots,\lambda_n} & m_{22\lambda_1,\lambda_2,\ldots,\lambda_n} & m_{23\lambda_1,\lambda_2,\ldots,\lambda_n} & m_{24\lambda_1,\lambda_2,\ldots,\lambda_n} \\ m_{31\lambda_1,\lambda_2,\ldots,\lambda_n} & m_{32\lambda_1,\lambda_2,\ldots,\lambda_n} & m_{33\lambda_1,\lambda_2,\ldots,\lambda_n} & m_{34\lambda_1,\lambda_2,\ldots,\lambda_n} \\ m_{41\lambda_1,\lambda_2,\ldots,\lambda_n} & m_{42\lambda_1,\lambda_2,\ldots,\lambda_n} & m_{43\lambda_1,\lambda_2,\ldots,\lambda_n} & m_{44\lambda_1,\lambda_2,\ldots,\lambda_n} \end{pmatrix} \quad (1)$$

The above Mueller Matrices of the sample are function of the optical properties of the medium, at different incident light wavelengths. By considering interrogation of the sample at two distinct wavelengths, one can obtain the $q^{th}$ measurement of the irradiance measurements, for two images as:

$$\vec{S}_{out,\lambda_1}(q) = M_{sys}\vec{S}_{in,\lambda_1} \quad (2)$$
$$= M_{LP2}M_{LR2}(q)M_{sample,\lambda_1}M_{LR1}(q)M_{LP1}(q)\vec{S}_{in}$$

$$\vec{S}_{out,\lambda_2}(q) = M_{sys}\vec{S}_{in,\lambda_2} \quad (3)$$
$$= M_{LP2}M_{LR2}(q)M_{sample,\lambda_2}M_{LR1}(q)M_{LP1}(q)\vec{S}_{in}$$

where $S_{out}(q)$ and $S_{in}$ are the Stokes parameters at the output and input of the optical system respectively, at two wavelengths; $M_{LP1}(q)$ and $M_{LP2}(q)$ are the Mueller Matrices of ideal polarizers with their transmission axes oriented along the horizontal x direction, and $M_{LR1}(q)$ and $M_{LR2}(q)$ are the Mueller Matrices of the quarter wave linear retarders in the polarization state generator and the polarization state analyzer, respectively, offered elsewhere. In general, $$M_{LP1} = M_{LP2} = \frac{1}{2}\begin{pmatrix} 1 & 1 & 0 & 0 \\ 1 & 1 & 0 & 0 \\ 0 & 0 & 0 & 0 \\ 0 & 0 & 0 & 0 \end{pmatrix} \quad (4)$$

$$M_{LR1}(q) = \begin{pmatrix} 1 & 0 & 0 & 0 \\ 0 & \cos^2 2\gamma q & \sin 2\gamma q \cos 2\gamma q & -\sin 2\gamma q_0 \\ 0 & \cos 2\gamma q \sin 2\gamma q & \sin^3 2\gamma q & \cos 2\gamma q \\ 0 & \sin 2\gamma q & -\cos 2\gamma q & 0 \end{pmatrix} \quad (5)$$

$$M_{LR2}(q) = \quad (6)$$
$$\begin{pmatrix} 1 & 0 & 0 & 0 \\ 0 & \cos^2 10\gamma q & \sin 10\gamma q \cos 10\gamma q & -\sin 10\gamma q_0 \\ 0 & \cos 10\gamma q \sin 10\gamma q & \sin^3 10\gamma q & \cos 10\gamma q \\ 0 & \sin 10\gamma q & -\cos 10\gamma q & 0 \end{pmatrix}$$

$$M_{sample} = \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix} \quad (7)$$

Substituting (4)-(7) into both (2) and (3) and carrying out the appropriate trigonometric transformations, one can show that the output irradiance is given by the first element of the output Stokes vector, $s_{0out}(q)$. The expression for the measured irradiance can be expanded and rewritten to produce terms that correspond to the Fourier series expansion $$s_{0,out}(q)_{\lambda_1} = I_q = \frac{\alpha_0}{2} + \sum_{n=1}^{12}(\alpha_n \cos 2\pi \gamma q + b_n \sin 2n\gamma q) \quad (8)$$

$$s_{0,out}(q)_{\lambda_2} = I_q = \frac{\alpha_0}{2} + \sum_{n=1}^{12}(\alpha_n \cos 2\pi \gamma q + b_n \sin 2n\gamma q) \quad (9)$$

for $\lambda_1$, and $\lambda_2$, respectively, and where $I_q$ is the measured irradiance, and the Fourier coefficients are a function of the sixteen elements of the Mueller matrix. These expressions can be inverted to obtain Mueller Sample Matrix elements in terms of the Fourier series coefficients. Therefore, a polarimetric Mueller-Matrix image difference can be defined as:

$$\begin{pmatrix} m_{11\lambda_2} & m_{12\lambda_2} & m_{13\lambda_2} & m_{14\lambda_2} \\ m_{21\lambda_2} & m_{22\lambda_2} & m_{23\lambda_2} & m_{24\lambda_2} \\ m_{31\lambda_2} & m_{32\lambda_2} & m_{33\lambda_2} & m_{34\lambda_2} \\ m_{41\lambda_2} & m_{42\lambda_2} & m_{43\lambda_2} & m_{44\lambda_2} \end{pmatrix} - \begin{pmatrix} m_{11\lambda_1} & m_{12\lambda_1} & m_{13\lambda_1} & m_{14\lambda_1} \\ m_{21\lambda_1} & m_{22\lambda_1} & m_{23\lambda_1} & m_{24\lambda_1} \\ m_{31\lambda_1} & m_{32\lambda_1} & m_{33\lambda_1} & m_{34\lambda_1} \\ m_{41\lambda_1} & m_{42\lambda_1} & m_{43\lambda_1} & m_{44\lambda_1} \end{pmatrix} \quad (10)$$

and vice-versa. Generally, one can generate n-Mueller matrices, corresponding to n-interrogating wavelengths. By subtracting the 16 Mueller matrix elements of one matrix, acquired at one wavelength by the correspondent one acquired at different wavelength, i.e., $m_{11\lambda_2}$-$m_{11\lambda_1}$, and so on, at predetermined combinations, significant information regarding the nature of the target and/or sample can be achieved. Typically, there are several experimental techniques to generate the full 16 element Mueller matrix. For example, a dual-rotating retarder Mueller matrix polarimeter technique, allows a complete measurement of all sixteen Mueller matrix elements through the Fourier analysis of the single detected signal.

(b) Stokes Polarization Parameters Spectral Differences,

Experimentally, there are several approaches to measure the Stokes parameters, namely: the "Classical Measurement Method-the Quarter-Wave", the "Measurement of the Stokes Parameters Method Using a Circular Polarizer", the "Fourier Analysis Using a Rotating Quarter-Wave Retarder Method", the "Rotating Retarder Polarimeter Based on the Polarimetric Measurement Matrix Method", and others. (See George C. Giakos, "Novel Molecular Imaging and Nanophotonics Detection Principles and Systems", presented May 13, 2005 at the International Workshop on Imaging Systems and Techniques, Niagara Falls).

For instance, the "Rotating Retarder Polarimeter Based on the Polarimetric Measurement Matrix Method", allows one to calculate the Stokes vector, $S_{out}(q)$ where $$S_{out}(q) = AS_{in} \quad (11)$$

where A is the Muller matrix describing the elements of the analyzer polarization of the phase retarder and the polarizer in front of the detector, including instrumental polarization, and polarization sensitivity of the detector, and, $S_{in}$=$(S_0, S_1, S_2, S_3)^T$ is the Stokes vector incident on the polarization state analyzer. Assuming linearity, the output intensity at the detector, i, is proportional to the incident intensity, according to:

$$i = \vec{A} \cdot \vec{S}_{inc} = a_0 s_0 + a_1 s_1 + a_2 s_2 + a_3 s_3 \quad (12)$$

where $\vec{A}=(a_0\ a_1\ a_2\ a_3)^t$ is an analyzer operator vector analogous to the Stokes vector. The incident Stokes vector, $S_{inc}$, on the polarization state analyzer, is determined by making a series of measurements $i_q$, changing the elements of the polarization state analyzer for each measurement. The intensity of the $q^{th}$ measurement is generally expressed as $$i_q = \vec{A}_q \cdot \vec{S}_{inc} \quad (13)$$

where $\vec{A}_q$ is the analyzer operator vector for the $q^{th}$ measurement. In general, the corresponding light intensities at the output of the detector, for Q measurements, are:

$$\begin{pmatrix} i_0 \\ i_1 \\ \vdots \\ i_{Q-1} \end{pmatrix} = \begin{pmatrix} a_{00} & a_{01} & a_{02} & a_{03} \\ a_{10} & a_{11} & a_{12} & a_{13} \\ \vdots \\ a_{(Q-1)0} & a_{(Q-1)1} & a_{(Q-1)2} & a_{(Q-1)3} \end{pmatrix} \begin{pmatrix} s_0 \\ s_1 \\ s_2 \\ s_3 \end{pmatrix} \quad (14)$$

where $a_{qj}$ is the $j^{th}$ element of $\vec{A}q$ for the $q^{th}$ measurement, where (j=0, 1, 2, 3), indicating the four Stokes parameters. Therefore, $$I_q = WS_{inc} \quad (15)$$

where W is the polarimetric measurement matrix.

Once the polarimetric measurement matrix is known, the estimated Stokes vector R can be deduced from the inverse of that matrix and, the measured intensities, through the polarimetric data reduction equation:

$$\hat{R} = W^{-1}I + UI \quad (16)$$

where U is the polarimetric data reduction matrix. The rows of W are the coefficients of $S_0$, $S_1$, $S_2$, and $S_3$, and I is the detected intensity for a sequence of polarization optics positions. The degree of polarization (DOP), degree of linear polarization (DOLP), degree of circular polarization (DOCP), ellipticity, and orientation also can be estimated in terms of Stokes parameters, as $$DOP = \frac{(S_1^2 + S_2^2 + S_3^2)^{1/2}}{S_0} \quad (17)$$

$$DOLP = \frac{(S_1^2 + S_2^2)^{1/2}}{S_0} \quad (18)$$

$$DOCP = \frac{S_3}{S_0} \quad (19)$$

$$e = \frac{b}{a} = \frac{s_3}{s_0 + \sqrt{s_1^2 + s_2^2}} \quad (20)$$

$$n = \frac{1}{2}\arctan\left[\frac{s_2}{s_1}\right] \quad (21)$$

$$\varepsilon = \sqrt{1 - e^2} \quad (22)$$

and $S_0$, $S_1$, $S_2$, $S_3$ are the Stokes vectors, e, η, and ε are the ellipticity, azimuth, and eccentricity, respectively. In general, multiple wavelengths can be utilized to interrogate the target and/or sample. As a result exploration and arithmetic manipulation of $S_0$, $S_1$, $S_2$, $S_3$, obtained at different wavelengths, such as subtraction (where the order of the operation can be inverted too), i.e., $(S_{0\ \lambda 2}-S_{0\ \lambda 1})$, $(S_{1\ \lambda 2}-S_{1\ \lambda 1})$, and so on, or addition, multiplication, division or combination of them, can enhance the image process, giving rise to Stokes polarization parameters differences and the like. An extension of the above concepts can lead to general relationships, such as:

$$(\sqrt{S_1^2+S_2^2+S_3^3}))_{\lambda_n} - (\sqrt{S_1^2+S_2^2 S_3^3}))_{\lambda_{n-1}} \quad (19)$$

$$(DOP)_{\lambda 2} - (DOP)_{\lambda 1} \quad (20)$$

$$(DOLP)_{\lambda 2} - (DOLP)_{\lambda 1} \quad (21)$$

$$(DOCP)_{\lambda 2} - (DOCP)_{\lambda 1} \quad (22)$$

$$(e)_{\lambda 2} - (e)_{\lambda 1} \quad (23)$$

$$(\eta)_{\lambda 2} - (\eta)_{\lambda 1} \quad (24)$$

$$(\epsilon)_{\lambda 2} - (\epsilon)_{\lambda 1} \quad (25)$$

where the arithmetical order of the operations can be also inverted.

In addition, imaging information of the target and/or sample is obtained by applying the Mueller matrix polar decomposition of the images at different wavelengths and forming their image differences, at least two different wavelengths. Subtraction of the diattenuation, retardance, depolarization power, and birefringence at distinct wavelengths, under multi-spectral interrogation of the target and/or sample can provide insightful structural and physiological information based on the difference of the attenuation of amplitude of the incident light, phase change difference, depolarizing potential of the target and/or sample difference, and phase shift difference, due to the variation of index of refraction, obtained at least two distinct wavelengths, respectively.

Figure 5:
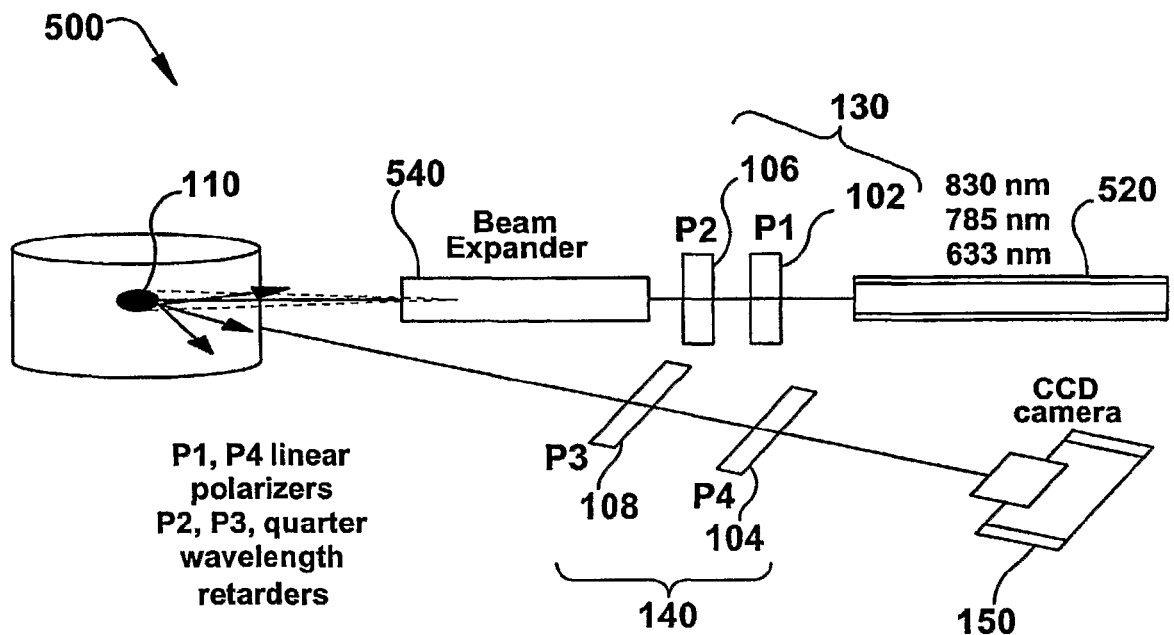
FIG. 5 is a multi-spectral Mueller matrix/Stokes parameter polarimeter according to another embodiment of the present invention.

In another embodiment, an imaging system according to the present invention is illustrated in FIG. 5. The system 500 of FIG. 5 is similar in nature to that of FIG. 1. However, a number of differences exist. First, the system of FIG. 5 does not utilize near-field optics 120. Additionally, FIG. 5 utilizes both a laser light source 520 and a beam expander 540. It should be noted that the embodiment of FIG. 5 is not limited to only the use of a laser light source as illustrated in FIG. 5. Rather, any suitable energy and/or light in accordance with the present invention can be utilized in conjunction with the embodiment of FIG. 5.

Figure 6:
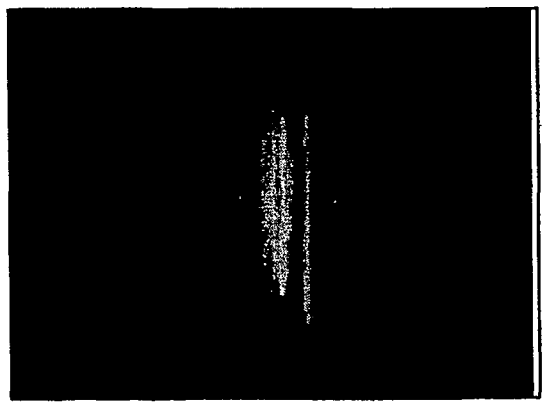
FIG. 6 is an image of a 1 mm diameter plastic wire embedded in 7 ml of water and 5 ml polar solution obtained using the apparatus of FIG. 5.
Figure 7:
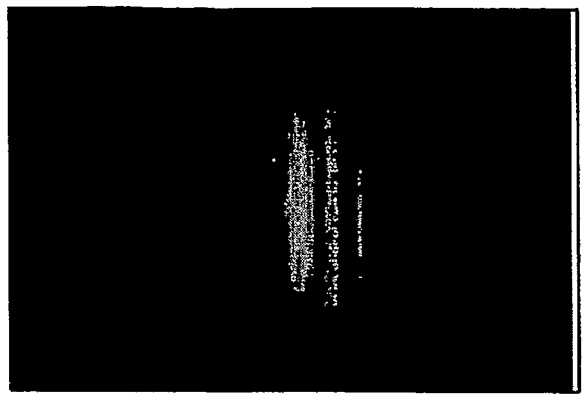
FIG. 7 is an image of a 1 mm diameter plastic wire embedded in 7 ml of water and 7 ml polar solution obtained using the apparatus of FIG. 5.
Figure 8:
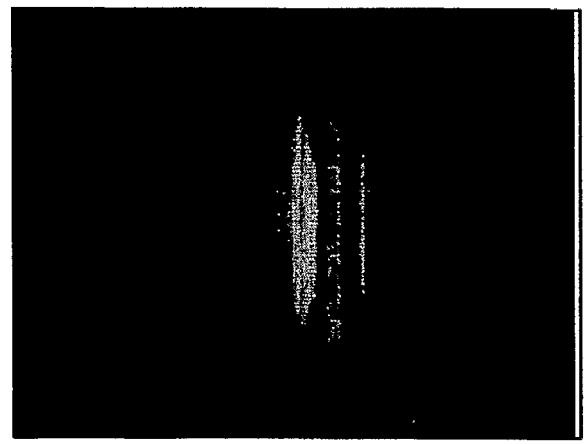
FIG. 8 is a DOLP image of a 1 mm diameter plastic wire embedded in 7 ml of water and 9 ml polar solution obtained using the apparatus of FIG. 5.
Figure 9:
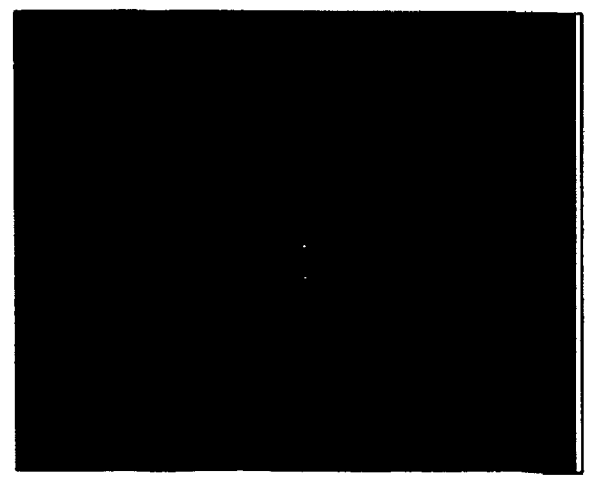
FIG. 9 is an image subtraction of the DOLP depicted in FIG. 8 minus the DOLP depicted on FIG. 6

The imaging system of FIG. 5 is used herein to generate the following experimental results when operated under backscattered geometry. A sample is interrogated by a 633 nm laser beam. The Rotating Retarder Polarimeter based on the Polarimetric Measurement Matrix Method is applied to estimate the DOLP A 1.9 cm test tube filled with 7 ml of water is incrementally filled with 1 ml of a polar solution (alcohol). A 1 mm plastic wire is suspended at the center of the test tube. DOLP images at various concentration of polar solution, are shown, in FIGS. 6 to 8. In FIG. 9, the image subtraction of the DOLP depicted in FIG. 8 minus the DOLP depicted on FIG. 6, is shown. This technique overall enhances the detection process. Several microstructures (bubbles) are visible on the surface of the wire as well as on the edge of the glass tube. The transmitter system consisted of a λ/4 retardation plate and a linear polarizer placed in the front of the laser beam. The receiver system consists of a λ/4 retardation plate and a linear polarizer placed in the front of a sixteen-bit thermo-electrically cooled CCD camera from Roper Scientific. For each image exposure, sixteen single frames are obtained, one at every 22.5° angle of rotation for a full 360° rotation range, and averaged together.

The physical and engineering principles of a novel Near-Field Scanning Microscopy System operating on multi-spectral, Muller Matrix polarimetric principles, for single-molecule imaging, tissue metabolic studies. In addition, the use of polar molecules, as new optical contrast agents for early cancer detection, is introduced and discussed. The presented multi-spectral polarimetric NSOM design principles may enhance the contrast and the detection process of the molecular cancer features, at the early stage. Further enhancement and background removal can be achieved by using Mueller matrix subtraction imaging at different optical wavelengths. On the other hand, the exploration and use of polar molecules as image contrast agents for medical imaging applications, both macroscopically and microscopically, in conjunction with multi-spectral polarimetric fluorescent imaging principles, can lead to the design of new high-contrast imaging technologies. Finally, the system can be implemented with Mueller Matrix/Stokes Polarization Parameters spectral difference capabilities, providing both high contrast and high noise rejection.

Devices/systems in accordance with the present invention have a wide variety of possible applications. Some exemplary applications include, but are not limited to, medical imaging, cancer detection, tumor detection, assessment of disease, follow-up medical imaging, margin detection, cellular imaging, physiological imaging, single molecule imaging, enhanced imaging systems, enhanced microscopy systems, molecular diagnostics and imaging, molecular analysis of a disease, drug development, proteomics, genetics, genomics, metabonomics, immunologic to expression profiling to imaging, pharmacogenomic markers predicting drug response and risk of adverse events, development of efficient sensors microfluidic micro/nanochips, LAB-on-a Chip, MEMS, nano-MEMS, analytical instrumentation, semiconductor inspection, material inspection, biology, biochemistry, biodefense, and industrial and/or military applications.

In addition the use of polar molecules and metallic nanostructures can be used for other applications, in conjunction with fluorescence, for enhanced underground, underwater detection of targets, mines, etc.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A multi-energy microscopy system comprising:
   (a) at least one energy source for irradiating a target and/or sample with at least one quantity of light and at least one quantity of energy, the at least one quantity of light comprising at least one wavelength of light and the at least one quantity of energy comprising at least one wavelength of energy, wherein the wavelength of the energy is either shorter or longer than the wavelength of the at least one quantity of light;
   (b) a polarization-state generator for generating a polarization state for each quantity of light, the polarization-state generator comprising at least one polarizer, each polarizer being adapted to polarize an individual wavelength before the one or more quantities of light enter a first waveplate;
   (c) a polarization-state receiver for evaluating a resulting polarization state of each of the one or more quantities of light following illumination of the target and/or sample, the polarization-state receiver comprising a second waveplate through which the one or more quantities of light are transmitted before entering at least one second polarizer;

(d) an image-capture device for capturing at least a first image and a second image of the target and/or sample irradiated by the at least one quantity of light and the at least one quantity of energy, the first image corresponding to an image of the target and/or sample generated from the wavelength of light and the second image corresponding to an image of the target and/or sample generated from the wavelength of energy;

(e) at least one near-field optics device;

(f) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (g) a processing unit for assigning a weighting factor to at least one of the first and second images and evaluating a weighted difference between the first and second images to generate a multi-wavelength image of the target and/or sample, wherein the microscopy system utilizes/implements Stark-effect imaging.

2. The system according to claim 1, wherein the first waveplate is a one-quarter (¼) waveplate.

3. The system of claim 1, wherein the second waveplate is a one-quarter (¼) waveplate.

4. The system of claim 1, wherein both the first and second waveplates are one-quarter (¼) waveplates.

5. A multi-energy near-field microscopy system comprising:

(i) at least two different light sources for illuminating a target and/or sample under two-photon and three-photon absorption-induced up-converted fluorescence;

(ii) a polarization-state generator for generating a polarization state in the light generated by the at least two light sources;

(iii) an image-capture device for capturing at least a first image and a second image of the target and/or sample illuminated by the at least two different light sources;

(iv) at least one near-field optics device;

(v) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (vi) a processing unit for assigning a weighting factor to at least one of the first and second images and evaluating a weighted difference between the first and second images to generate a multi-wavelength image of the target and/or sample, wherein the microscopy system utilizes near-field optics and implements Stark-effect imaging.

6. A multi-energy far-field microscopy system comprising:

(i) at least one light source for illuminating a target and/or sample with at least one quantity of light, the at least one quantity of light comprising at least two wavelengths of light, a first wavelength and a second wavelength, the second wavelength being different than the first wavelength;

(ii) a polarization-state generator for generating a polarization state for each quantity of light, the polarization-state generator comprising at least one polarizer, each polarizer being adapted to polarize an individual wavelength before the one or more quantities of light enter at least one first waveplate;

(iii) a polarization-state receiver for evaluating a resulting polarization state of each of the one or more quantities of light following illumination of the target and/or sample, the polarization-state receiver comprising at least one second waveplate through which the one or more quantities of light are transmitted before entering at least one second polarizer;

(iv) an image-capture device for capturing at least a first image and a second image of the target and/or sample illuminated by the at least one quantity of light, the first image corresponding to an image of the target and/or sample generated from the first wavelength component of the at least one quantity of light and the second image corresponding to an image of the target and/or sample generated from the second wavelength component of the at least one quantity of light;

(v) at least one near-field optics device;

(vi) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and (vii) a processing unit for assigning a weighting factor to at least one of the first and second images and evaluating a weighted difference between the first and second images to generate a multi-wavelength image of the target and/or sample.

7. The system according to claim 6, wherein there is one light source and the light source is capable of simultaneously generating a quantity of light having at least two discrete wavelengths of light.

8. The system according to claim 6, wherein there is one light source and the light source is capable of sequentially generating a quantity of light having at least two discrete wavelengths of light.

9. The system according to claim 6, wherein there is at least two light sources and each light source is capable of generating a quantity of light having one discrete wavelength of light.

10. The system according to claim 6, wherein the image-capture device is a light image-capture device.

11. The system according to claim 10, wherein the light image-capture device is an electro-optical device.

12. The system according to claim 1, wherein the electro-optical device is positioned in optical alignment with the polarization-state receiver to capture the first and second images.

13. The system according to claim 6, wherein the at least one light source comprises at least one laser.

14. The system according to claim 6, wherein the at least one light source is configured to emit energy in a planar geometry, fan-beam geometry, pointwise irradiation, or any combination thereof.

15. The system according to claim 6, wherein the first and second waveplates are each a quarter-wave retarder.

16. The system according to claim 15, wherein the quarter-wave retarders forming the first and second waveplates are rotated at an angular-velocity ratio of 5:1.

17. The system according to claim 6, wherein the polarization-state generator and the polarization-state receiver are generally linearly aligned on opposite sides of the target and/or sample.

18. The system according to claim 6, wherein the polarization-state receiver is positioned to evaluate the resulting polarization state of each quantity of light reflected by the target and/or sample.

19. The system according to claim 6, further comprising a computer readable memory for storing information to be used by the processing unit for determining a suitable wavelength for each quantity of light.

20. The system according to claim 19, wherein the processing unit comprises an artificial fuzzy neural network that uses information stored in the computer readable memory to determine a suitable wavelength for each quantities of light for the conditions at a time when the multi-energy image is to be generated.

21. The system according to claim 6, wherein the image-capture device converts the first captured image into a first Mueller matrix of the target and/or sample and the second captured image into a second Mueller matrix of the target and/or sample in order to permit processing, comparison, combination and/or arithmetical manipulation of the Mueller matrices from first and second images.

22. The system according to claim 6, wherein the image-capture device converts the first captured image into a first Stokes parameter image of the target and/or sample and the second captured image into a second Stokes parameter image of the target and/or sample in order to permit processing, comparison, combination and/or arithmetical manipulation of the DOP, DOLP, DOCP, ellipticity, and the Mueller matrices from first and second images that are acquired at different wavelengths.

23. A multi-energy near-field microscopy system comprising:
(A) at least one light source for illuminating a target and/or sample with at least one quantity of light, the at least one quantity of light comprising at least two wavelengths of light, a first wavelength and a second wavelength, the second wavelength being different than the first wavelength;
(B) a polarization-state generator for generating a polarization state for each quantity of light, the polarization-state generator comprising at least one polarizer, each polarizer being adapted to polarize an individual wavelength before the one or more quantities of light enter through at least one rotating one-quarter ($\frac{1}{4}$) waveplate linear retarder;
(C) a polarization-state receiver for evaluating a resulting polarization state of each of the one or more quantities of light following illumination of the target and/or sample, the polarization-state receiver comprising at least one second rotating one-quarter ($\frac{1}{4}$) waveplate linear retarder through which the one or more wavelengths of light are transmitted before entering at least one second polarizer;
(D) an image-capture device for capturing at least a first image and a second image of the target and/or sample illuminated by the at least one quantity of light, the first image corresponding to an image of the target and/or sample generated from the first wavelength of light and the second image corresponding to an image of the target and/or sample generated from the second wavelength of light, wherein the image-capture device receives and/or generates for each of the at least first and second images at least 16 individual polarization-state measurements;
(E) at least one near-field optics device;
(F) at least one of a polar contrast agent, a fluorescent particle, a nanoparticle or a combination of any two or more thereof, wherein the one or more polar contrast agents, one or more fluorescent particles, one or more nanoparticles, or combination thereof is/are administered to the target and/or sample or the purpose of enhancing the contrast between different areas or regions of the target and/or sample; and
(G) a processing unit for comparing the at least 16 individual polarization state measurements from the at least first and second images,
wherein the microscopy system utilizes near-field optics and implements Stark-effect imaging.

24. The system according to claim 23, wherein the 16 individual polarization state measurements from each image are averaged together by the processing unit to form average polarimetric images corresponding individually to at least the first and second images.

25. The system of claim 24, wherein the first Mueller matrix, DOP DOLP DOCP and ellipticity of the polarimetric image of the target and/or sample and the second Mueller matrix, DOP DOLP DOCP and ellipticity of the polarimetric image of the target and/or sample are subtracted from one another to obtain a weight spectral image difference of the target and/or sample obtained at two different wavelengths.

26. The system according to claim 23, wherein the 16 individual polarization state measurements from each image are used to generate a Mueller matrix for one individual wavelength of light.

* * * * *